United States Patent
Brand et al.

(10) Patent No.: US 6,606,989 B1
(45) Date of Patent: Aug. 19, 2003

(54) PRECISE ADMINISTRATION OF A MEDICATED AEROSOL VIA THE LUNGS

(75) Inventors: Peter Brand, Gauting (DE); Titus Selzer, Munich (DE); Holger Schulz, Landsberg (DE); Christa Roth, Eschborn (DE); Joachim Heyder, Munich (DE)

(73) Assignee: GSF-Forschungszentrum fur Umwelt und Gesundheit GmbH (DE)

( * ) Notice: Subject to any disclaimer, the term of this patent is extended or adjusted under 35 U.S.C. 154(b) by 0 days.

(21) Appl. No.: 09/423,909

(22) PCT Filed: May 8, 1998

(86) PCT No.: PCT/EP98/02703

§ 371 (c)(1),
(2), (4) Date: Apr. 3, 2000

(87) PCT Pub. No.: WO98/52633

PCT Pub. Date: Nov. 26, 1998

(30) Foreign Application Priority Data

May 16, 1997 (DE) .......................................... 197 20 701

(51) Int. Cl.$^7$ ............................................. A61M 11/00
(52) U.S. Cl. ............................. 128/200.16; 128/200.21
(58) Field of Search ....................... 128/200.16, 200.21, 128/203.13; 600/538

(56) References Cited

U.S. PATENT DOCUMENTS

| | | | |
|---|---|---|---|
| 2,215,241 A | 9/1940 | Eichelberger et al. | |
| 2,616,283 A | 11/1952 | Branstrator et al. | |
| 3,446,692 A | 5/1969 | Turnbull | |
| 3,812,854 A | * 5/1974 | Michaels et al. | 128/200.16 |
| 3,872,641 A | 3/1975 | Falkenberg | |
| 3,921,637 A | 11/1975 | Bennie et al. | 128/203.15 |
| 4,057,944 A | 11/1977 | Wyatt, Jr. et al. | |
| 4,057,945 A | 11/1977 | Kessler | |
| 4,114,608 A | * 9/1978 | Russo | 600/538 |
| 4,268,460 A | * 5/1981 | Boiarski et al. | 128/200.16 |
| 4,431,691 A | 2/1984 | Greenlee | |
| 4,986,269 A | * 1/1991 | Hakkinen | 128/200.21 |
| 5,033,593 A | 7/1991 | Kazuhito | |
| 5,063,922 A | * 11/1991 | Hakkinen | 128/200.16 |
| 5,080,093 A | * 1/1992 | Raabe et al. | 128/200.21 |
| 5,280,784 A | * 1/1994 | Kohler | 128/200.21 |
| 5,377,473 A | 1/1995 | Narayan et al. | |
| 5,507,281 A | 4/1996 | Kuhnel et al. | 128/203.15 |
| 5,543,204 A | 8/1996 | Ray | |
| 5,713,349 A | * 2/1998 | Keaney | 128/204.21 |

FOREIGN PATENT DOCUMENTS

| | | |
|---|---|---|
| DE | 28 09 255 A1 | 9/1978 |
| DE | 3610002 | 3/1986 |
| DE | 3827636 | 8/1988 |
| DE | 3901963 | 1/1989 |
| DE | 69203372 | 4/1992 |
| DE | 43 00 880 A1 | 7/1994 |
| EP | 0642802 | 8/1994 |
| FR | 2 604 093 | 3/1988 |
| GB | 2164569 | * 3/1986 |
| WO | 96/13293 | 5/1996 |

* cited by examiner

Primary Examiner—Aaron J. Lewis
(74) Attorney, Agent, or Firm—Fish & Richardson P.C.

(57) ABSTRACT

A device for administration of a medicated aerosol via the lungs consists of an inhalation mouthpiece 11, with an associated adjustable vaporizer 12, and of a compressed-air control valve 14 through which a pre-settable (13) volumetric flow of compressed air can be discharged to the vaporizer 12 containing the liquid medicament throughout a settable period of time. For operation of the device an electronic controller is provided on which the vaporizing period of the vaporizer and a pause interval can be set, with provisions being made for triggering the beginning of the vaporizing operation by means of a pressure sensor responsive to a suction pressure in the mouthpiece.

20 Claims, 1 Drawing Sheet

PRECISE ADMINISTRATION OF A MEDICATED AEROSOL VIA THE LUNGS

The present invention relates to a device for administration of a medicated aerosol via the lungs in accordance with the introductory clause of Patent claim 1.

The use of the respiratory tract for the administration of medicaments is gaining an ever-increasing importance. In this approach not only the application of new medicaments producing local effects for the treatment of pulmonary diseases is being developed, but also new therapeutic strategies are being designed which employ the lungs as the organ through which substances enter the body which produce systemic effects.

For the employment of the inhalation canal for the administration of medicaments continuously growing demands are made on the quality of the process of inhalation, which cannot be satisfied by the devices presently available in the market. For instance, it is necessary that the dosage of the medicament, which the physician has prescribed, will be administered as precisely as possible and in a reproducible manner, with the administered dose and its reproducibility depending substantially on the so-called respiration manoeuvre. The term "respiration manoeuvre" is to be understood to encompass the aerosol volume inhaled and the respiratory flow by which the patient performs the inhalation. With an appropriate selection of the respiration manoeuvre and the vaporiser or by matching the applied respiratory manoeuvre with the used vaporiser (particle size) the location of deposition of the medicament in the lungs could be selectively influenced so as to provoke a predominantly central or predominantly peripheral administration of the pharmaceutical.

A device of the general type outlined by way of introduction is disclosed already in the French Patent FR-A-2604093. What must be considered to be a disadvantage in this device is the fact that, on the one hand, the handling is complex and that, on the other hand, an administration dependent on the individual respiratory manoeuvre cannot be performed or realised only insufficiently.

As in every-day clinical routine the respiratory manoeuvre performed by the patient can usually be influenced only to a small extent or as the respiratory manoeuvre actually performed is almost entirely beyond control by the physicians a precise pre-determination of the respiratory volume and the respiratory flow in the inhalation of therapeutic aerosol were desirable because this would entail a substantial improvement of the inhalation therapy and its reproducibility. As a consequence, the administered dose could be estimated with a higher precision, with a precise observation of a particular respiratory manoeuvre, whilst at the same time savings in terms of costs could be achieved as well when particularly expensive pharmaceuticals are administered.

The present invention is therefore based on the problem of responding to the needs outlined in the foregoing with a device having a functionally simple design.

In accordance with this invention this problem is solved by the features defined in the claims. Preferred features providing an expedient improvement of the invention are also defined in the claims.

The inventive device expediently consists of an inhalation mouthpiece, an associated adjustable vaporiser and a compressed-air control valve through which a pre-settable volumetric flow of compressed air which can be supplied to the vaporiser containing the liquid medicament during an adjustable period of time, with a pressure sensor being provided for triggering the beginning of the vaporising operation of the vaporiser.

With the inventive device the patient is therefore enabled, with simple means, to inhale a precisely predetermined volume of a pharmaceutical substance at a precisely predetermined respiratory flow. With this device the separate air supply, which is already envisaged for therapeutic vaporisers in the clinical every-day routine, is expediently controlled in such a way that only a predetermined volume of air is output to the vaporiser at a predetermined flow rate. In accordance with the present invention hence the air of the vaporiser is adjusted to a pre-settable intensity of the volumetric flow, which the patient cannot take an influence on so that a constant flow will be achieved. The flow of supplied air is preferably turned on by an electronic controller over an invariably set period of time so as to achieve the administration of a precisely pre-determined air volume. On account of the length of a breathing pause, which can be determined with a special design of the invention, the total deposition of the medicament is expediently increased whilst the inter-individual variability of the deposited quantity is reduced.

For use of the device in practical application it is moreover expedient to provide a pressure gauge responsive to a suction pressure in the inhalation mouthpiece for triggering the beginning of the vaporising operation of the vaporiser In accordance with a preferred configuration a controller is disposed upstream of the adjustable vaporiser for maintaining the volumetric flow constant, with a flow meter being preferably arranged downstream of the controller for control of a predetermined volumetric flow, which flow meter comprises a floating body in a specific embodiment. These provisions contribute expediently to an ensured controlled inhalation of therapeutic aerosols by means of the inventive device.

According to a preferred embodiment of the invention, the device comprises an electrical controller to control its operation, with a vaporising period and a pause interval being adjustable on the controller and with the electronic controller preferably including a visible and/or audible pause signal to indicate the pause between inhalation and exhalation, preferably in the form of a light-emitting diode. Moreover, the number of the vaporising periods can expediently be set in the form of a number of respiration cycles.

As far as the configuration of the vaporiser is concerned either a design in the form of a nozzle-type vaporiser with a separate compressed-air supply is envisaged, which can be turned on and off by means of the compressed-air control valve, with the separate compressed-air supply for the nozzle-type vaporizer being preferably branched off between the compressed-air control valve and the flow meter.

In an alternative design the vaporiser may be configured as ultrasonic transducer issuing high-frequency signals which can be directly controlled by the electronic controller.

The compressed-air control valve is preferably designed as solenoid valve, and a pressure reducer and a pressure gauge are arranged upstream of the control valve for adaptation to the individual compressed-air conditions.

In accordance with the invention a wide range of respiratory manoeuvres can expediently be opened up for medical applications with the simultaneous selection of the respiratory flow and the inhaled volume, with the opportunity to take an influence on the location of deposition in the lung in the desired manner. It is thus possible for the first time to deposit medicaments which are intended, for instance, to produce their effects in central areas of the lungs actually at the envisaged points.

Another advantage of the inventive device consists in the aspect that it permits an improvement of a routine performance of inhalations on patients in the clinical environment because, by virtue of the envisaged respiration triggering of inhalation, a patient will not encounter any problems with respect to the synchronisation of the start of operation of the vaporiser and hence the beginning of the inhalation operation. It is moreover expediently possible to reduce errors in inhalation substantially, which are due to improper handling of the vaporiser.

The invention will now be described in more details in the following with reference to the attached drawing wherein.

Figure 1:
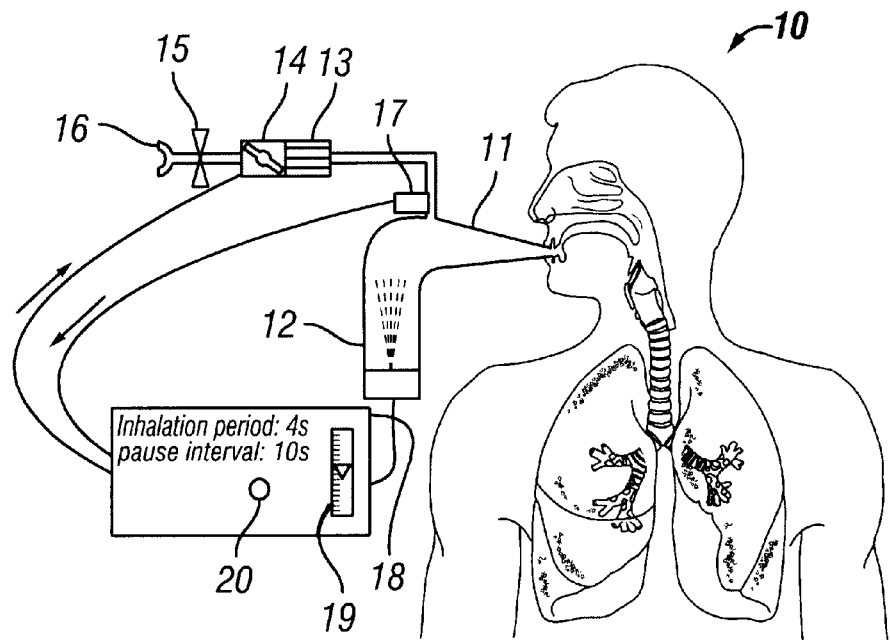
FIG. 1 is a schematic view of one embodiment of an inventive Device.

FIG. 1 illustrates a schematic view of the interaction of the individual components of an inventive device 10 with reference to a particular embodiment. The device 10 for the administration of a medicated aerosol through the lung consists of an inhalation mouthpiece 11 with an associated vaporiser 12 which can be adjusted in terms of its operating phases as well as intensity/frequency. A volumetric flow controller 13, a compressed-air control valve 14, which is preferably configured as solenoid valve, a pressure reducer 15 and a compressed-air inlet 16 are disposed to be in flow communication with the inhalation mouthpiece 11. The reference numeral 17 denotes a pressure sensor which is responsive to a suction pressure in the mouthpiece for triggering the beginning of the vaporising operation of the vaporiser 12.

An electronic controller 18 is functionally connected to the compressed-air control valve 14, the pressure sensor 17 and the vaporiser 12. The electronic controller 18 is schematically represented as housing block which is additionally provided with an optical display of a flow meter 19 for checking the inhalatory flow, for instance over a range of values from 0 to 1000 cm$^3$/s. The volumetric flow controller 13 serves to maintain the inhalatory flow constant over a range from 0 to 1000 cm$^3$/s, for example. The compressed-air valve 14 is preferably designed as solenoid valve which switches the air supply.

Moreover, the inhalation period, the pause interval and the number of breathing cycles can be set on the electronic controller 18 in a manner not illustrated here, with a light-emitting diode 20 being provided to issue a pause signal.

Figure 2:
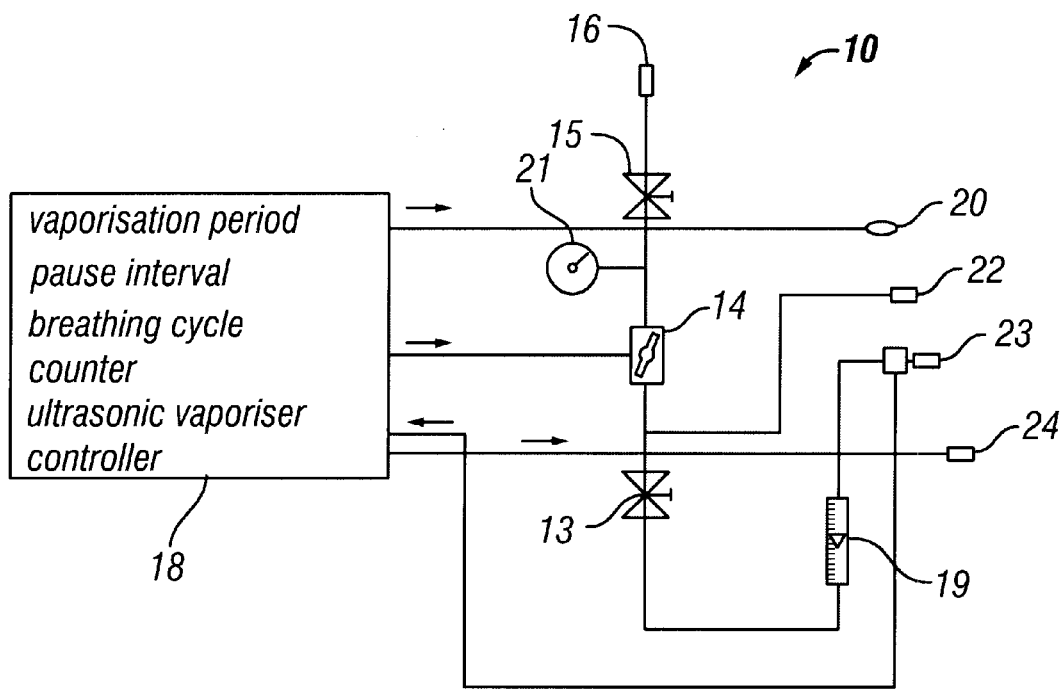
FIG. 2 is a schematic diagram showing the components of the Embodiment of the invention according to FIG. 1.

A pressure gauge 21, which is schematically shown in FIG. 2, is provided between the pressure reducer 15 and the solenoid valve 14 for setting the operating pressure of the vaporiser, for instance over a range of values from 0 to 2 bar, as a supplement to the embodiment according to FIG. 1. Moreover, a compressed-air coupler 22 is provided in this embodiment, which stops automatically and serves to supply the nozzle of a vaporiser which is configured here as a nozzle-type vaporiser. For connection of the vaporiser 12 as such an adapter is illustrated by the reference numeral 23 whereas the numeral 24 denotes a signalling line for switching a vaporiser configured in the form of an ultrasonic vaporiser.

The individual functions which can be set, such as vaporising period or inhalation time, the pause interval and the ultrasonic vaporiser control, are mentioned in text form in the block of the electronic controller 18, with a breathing cycle counter being included for detection of the breathing cycles.

For use of the inventive device 10 initially the nominal flow of inhalation is controlled by means of the flow meter 19, which includes a floating body, and then set to the desired amount at the volumetric flow controller 13 or the controller, respectively, which maintains the flow constant. Then the desired inhalation period is set via keys on the electronic controller 18, which are not illustrated here, e. g. within a range from 0 to 20 seconds. The inhaled volume then derives from the inhalation period and the flow of inhalation. The desired duration of the pause interval is equally set on the controller 18 via keys not illustrated here, for instance within a range from 9 to 20 seconds. Additionally, the breathing cycle counter is set to zero.

Following these preparations, inhalation can now be performed in a way that the patient sucks at the mouthpiece 11, which causes the pressure sensor 17 to respond and start inhalation automatically. The vaporiser 12 is supplied with compressed air throughout the pre-selected inhalation period, and the desired medicament is discharged in the form of a medicated aerosol from the mouthpiece 11 at a preselected flow rate. Upon expiration of the inhalation period the compressed-air supply is interrupted so that the patient cannot continue inhalation. The light-emitting diode 20 signals to the patient that he or she should hold his or her breath. As soon as the pause interval has elapsed the pause interval LED 20 is extinguished, the patient exhales and the breathing cycle counter is incremented. Now the device is ready for the next inhalation cycle.

Another possibility of adjusting the vaporising operation in a nozzle-type vaporiser consists in controlling the compressed air supply which is branched off between the solenoid valve 14 and the flow meter controller 13. When an ultrasonic vaporiser is used the required high-frequency signal can be separately controlled in an appropriate manner.

What is claimed is:

1. A device for deposition of a medicament in a liquid form in the lungs, comprising:

an inhalation mouthpiece;

a pressure sensor responsive to a suction pressure in said mouthpiece to produce a triggering signal;

an adjustable vaporiser coupled to the inhalation mouthpiece and to receive a nozzle flow and a separate compressed-air flow, which vaporizer contains the medicament and delivers the vaporised medicament to the mouthpiece for a vaporising period in response to a vaporising signal;

a compressed-air control valve, which, in response to a valve signal, opens to allow the nozzle flow and the separate compressed-air flow to enter the vaporiser throughout the vaporising period to provide a predetermined inhaled volume, and closes at the end of the vaporising period to stop the nozzle flow and the separate compressed air flow;

a volumetric flow controller coupled to the compressed-air control valve to preset a determined quantity of a volumetric flow of the nozzle flow;

a flow meter disposed downstream of said volumetric flow controller for control of a predetermined volumetric flow; and an electronic controller connected to receive the triggering signal from the pressure sensor to produce the valve signal and the vaporising signal, said electronic controller being configured with the settable vaporising period and a settable pause interval and operable to set the varporing period of the adjustable vaporiser to an invariable value from opening of the compressed-air control valve and causes a predetermined volume for each respiratory manoeuvre at the inhalation mouthpiece.

2. The device of claim 1 further comprising a compressed-air coupler connecting to a compressed-air line which is branched off between the compressed-air control valve and the volumetric flow controller for carrying the separate compressed air flow, wherein the compressed-air coupler stops the separate compressed air flow from entering the vaporiser if the vaporiser is configured as an ultrasonic transducer.

3. The device according to claim 1, wherein said volumetric flow controller is disposed upstream of said vaporiser which is adapted to be set in terms of time, for maintaining the volumetric flow constant.

4. The device according to claim 1, wherein said flow meter includes a floating body.

5. The device according to claim 1, wherein said electronic controller comprises a visible and/or audible pause signal to indicate the pause period between inhalation and exhalation.

6. The device according to claim 5, wherein said pause signal is generated by a light-emitting diode.

7. The device according to claim 1, wherein the number of vaporising periods is set in a form of a number of breathing cycles.

8. The device according to claim 1, wherein said vaporiser is configured in a form of an ultrasonic transducer issuing high frequency signals which are controllable by means of said electronic controller.

9. The device according to claim 1, wherein said compressed-air control valve is configured in the form of a solenoid valve.

10. The device according to claim 1 further comprising a pressure reducer and a pressure gauge disposed upstream of said compressed-air control valve.

11. A device for deposition of a medicament in a liquid form in the lungs, comprising:

an inhalation mouthpiece;

a pressure sensor responsive to a suction pressure in said mouthpiece to produce a triggering signal;

an adjustable vaporiser coupled to the inhalation mouthpiece and to receive a nozzle flow, which vaporizer contains the medicament and issues high frequencies to deliver the vaporised medicament to the mouthpiece for a vaporising period in response to a vaporising signal;

a compressed-air control valve, which, in response to a valve signal, opens to allow the nozzle flow to enter the vaporiser throughout the vaporising period to provide a predetermined inhaled volume, and closes at the end of the vaporising period to stop the nozzle flow; a volumetric flow controller coupled to the compressed-air control valve to preset a determined quantity of a volumetric flow of the nozzle flow;

a flow meter disposed downstream of said volumetric flow controller for control of a predetermined volumetric flow; and an electronic controller that receives the triggering signal from the pressure sensor to produce the valve signal and the vaporising signal, said electronic controller being configured with the settable vaporising period and a settable pause interval and controlling the high frequencies issued by the vaporizer and operable to set the varporing period of the adjustable vaporiser to an invariable value from opening of the compressed-air control valve and causes a predetermined volume for each respiratory manoeuvre at the inhalation mouthpiece.

12. The device according to claim 11, wherein said volumetric flow controller is disposed upstream of said vaporiser which is adapted to be set in terms of time, for maintaining the volumetric flow constant.

13. The device according to claim 11, wherein said electronic controller comprises a visible and/or audible pause signal to indicate the pause period between inhalation and exhalation.

14. The device according to claim 11, wherein said compressed-air control valve is configured in the form of a solenoid valve.

15. The device according to claim 11 further comprising a pressure reducer and a pressure gauge disposed upstream of said compressed-air control valve.

16. A method for administration of a medicated aerosol via lungs, comprising:

providing an adjustable vaporiser to vaporize a medication to be delivered through a mouthpiece for inhalation; providing a controllable air flow via a compressed-air control valve to the adjustable vaporiser to produce the medicated aerosol and direct the medicated aerosol to the mouthpiece;

using a volumetric flow controller coupled to the compressed-air control valve to preset a determined quantity of a volumetric flow;

using a flow meter downstream of the compressed-air control valve to control the air flow at a constant flow rate;

using a pressure sensor at the mouthpiece to produce a triggering signal upon sensing a suction at the mouthpiece;

in response to the triggering signal, turning on the adjustable vaporizer to operate and opening the compressed-air control valve to allow the controllable air flow into the adjustable vaporiser, for a predetermined invariable vaporizing period; and turning off both the adjustable vaporiser and the compressed-air control valve at the end of the vaporizing period to provide a predetermined constant volume of the medication for different respiratory manoeuvres.

17. The method as in claim 16, further comprising:

using an indicator light to signal to a patient to hold a breath after an inhalation; and after expiration of a predetermined pause interval, using the indicator light to signal to the patient to exhale and thus to begin a subsequent inhalation cycle.

18. The method as in claim 16, further comprising adjusting a flow rate of the controllable air flow to change the predetermined constant volume of the medication.

19. The method as in claim 16, further comprising adjusting the predetermined invariable vaporizing period to change the predetermined constant volume of the medication.

20. The method as in claim 16, further comprising:

using the flow meter to initially control the air flow prior to setting the volumetric flow controller;

subsequently setting the volumetric flow controller to a desired setting; and using an electronic controller to set the predetermined invariable vaporizing period to await the triggering signal to begin delivery of the medicated aerosol.

* * * * *